United States Patent [19]

Yatsurugi et al.

[11] 3,982,912
[45] Sept. 28, 1976

[54] METHOD FOR PREPARATION OF AN IMPROVED K-A TYPE ZEOLITE AND FOR SEPARATION BY ADSORPTION POLAR AND NON-POLAR MOLECULES

[76] Inventors: Yoshifumi Yatsurugi, 6-507, 7-ban, 2-chome, Tsujido-Nishikaigan, Fujisawa, Kanagawa; Tatsuo Kuratomi, 2-18, 4-chome, Hamatake, Chigasaki, Kanagawa; Tetsuo Takaishi, 1461-251, Nagae, Hayamacho, Miuragun, Kanagawa, all of Japan

[22] Filed: May 6, 1974

[21] Appl. No.: 467,123

Related U.S. Application Data

[63] Continuation-in-part of Ser. No. 221,469, Jan. 27, 1972, abandoned, and a continuation-in-part of Ser. No. 368,966, June 11, 1973.

[30] Foreign Application Priority Data

Mar. 31, 1971 Japan.............................. 46-18697
Oct. 2, 1971 Japan.............................. 46-76817

[52] U.S. Cl....................................... 55/35; 55/68; 55/75

[51] Int. Cl.²...................................... B01D 15/00
[58] Field of Search........................... 55/35, 68, 75; 208/DIG. 2; 252/455 Z; 423/328

[56] References Cited
UNITED STATES PATENTS 3,785,122   1/1974   Vatsudual et al....................... 55/75

Primary Examiner—John Adee
Attorney, Agent, or Firm—Otto John Munz

[57] ABSTRACT

A novel type of zeolite is obtained by replacing ion-exchangeable active cations in A-type zeolite with potassium ions and divalent cations at 33.3 to 83.3% and 16.7 to 66.7%, respectively to combine into the total of 100%. This zeolite is effective for separation of a mixture consisting of non-polar molecules and polar molecules having the adsorption effective cross-section less than 5 A. For instance, monosilane and phosphine, both of which are adsorbed by the conventional Ca—A type zeolite, can be separated by the novel K—A type zeolite which adsorbs phosphine.

4 Claims, 2 Drawing Figures

METHOD FOR PREPARATION OF AN IMPROVED K-A TYPE ZEOLITE AND FOR SEPARATION BY ADSORPTION POLAR AND NON-POLAR MOLECULES

CROSS-REFERENCES TO RELATED APPLICATIONS

This is a continuation-in-part application to copending patent applications Ser. Nos. 221,469, filed Jan. 27, 1972 now abandoned and 368,966, filed Jun. 11, 1973, for: PROCESS FOR PREPARATION OF IMPROVED NOVEL K-A TYPE ZEOLITE AND METHOD FOR SEPARATING BY ADSORPTION OF MIXTURES USING THE SAME
and for: PROCESS FOR PREPARING 4,5 A ZEOLITE AND METHOD FOR SEPARATING MIXTURES USING SAME
respectively, and priorities thereof and of corresponding Pat. Nos. 18697/46 filed in Japan on Mar. 31, 1971 and 76817/46 filed in Japan on Oct. 2, 1971 are claimed under 35 U. S.C. 120 and under the Convention, respectively.

BACKGROUND OF THE INVENTION

1. Field of the Invention

A process for the preparation of a K-A type zeolite, and separation by adsorption of mixtures using zeolite or a molecular sieve (Class 23, Subclass 113, and Class 55, Subclass 74.)

2. Description of the Prior Art

In the prior art, a variety of zeolites, natural and artificial, have been industrially used. Artificial zeolites are preferred because of their uniform properties, and a typical one is the A-type zeolite. A-type zeolite is represented by its sodium salt having the chemical composition of $Na_{12}(AlO_2.SiO_2)_{12}(NaAlO_2)_\delta \cdot XH_2O$, wherein $0 \leq \gamma \leq 1$, and X is an integer. Twelve sodium ions in the formula are chemically active and readily exchanged by other cations. Those A-type zeolites in which sodium ions are replaced by potassium ions and calcium ions are called K-A type zeolite and Ca-A type zeolite, respectively, and an unreplaced one is called Na-A type zeolite. The A-type zeolite varies in the size of pore openings for adsorption depending on the kind of cations exchanged. For instance, Na-A type zeolite, Ca-A type zeolite, and K-A type zeolite adsorb selectively molecules having diameters of 4A, 5A and 3A, or less respectively, and they are conventionally defined as 4A zeolite, 5A zeolite, and 3A zeolite. This characteristic is attributed to the crystal structure of A-type zeolite. That is, in the case of Na-A type zeolite, eight 6-membered oxygen rings and three 8-membered oxygen rings contained in the unit lattices are occupied by eight and four sodium ions, respectively, and the adsorption property is affected by the kind of ion which exchanges the four sodium ions in the 8-membered oxygen ring. The detailed physico-chemical mechanism of cation exchange by the A-type zeolite has not been elucidated.

The prior art is represented by U.S. Pat. Nos.
3,078,645 for: HYDROCARBON SEPARATION, and
3,078,636 for: UNSATURATED HYDROCARBON SEPARATION both issued Feb. 26, 1963 to R. M. Milton,
3,056,654 for: PROCESS OF MAKING CRYSTALLINE ZEOLITE K-G issued Oct. 2, 1962 to BARRER et al. and the present inventors own prior U.S. Pat. No. 3,785,122 of Jan. 15, 1974, entitled to the benefits of the same priorities as the present case. Barrer et al corresponds to the rhombohedral crystaline system with a unit cell edge equal to 9.52A. The A-type zeolite used in the present invention differs substantially from the K-G zeolite in its characteristics. For better understanding of the difference, reference is made to "Silicate Science", Vol. IV, *Academic Press*, 1966, pages 500–501.

In addition Barrer et al recites a zeolite of substantially less metal content than of the instant invention, causing substantial changes in the molecular formula. Further Barrer et al does not recognize the expansion of the intracrystalline voids by exchange of calcium ion for sodium ion.

U.S. Pat. No. 3,078,645 discloses a prior art method which effects conversion from the Na—A type zeolite to the Ca—A type zeolite by exchange of about 20 – 40% of calcium.

U.S. Pat. No. 3,078,636 deals with separation of unsaturated hydrocarbon in which conventional A-type zeolites are used and teaches adsorption of saturated hydrocarbon and nitrogen, wherein the separation of the gas depends merely on discrepancy of the absorbility and it does not and can not utilize sieving action.

SUMMARY OF THE INVENTION

The inventors discovered that the adsorption property of zeolite and particularly the duration of the adsorption vary extremely, depending on the kind of cations exchanged. The A-type zeolite used in accordance with the present invention is represented by the chemical formula $Na_2O:Al_2O_3:1.85 SiO_2:XH_2O$, wherein X is an integer. The ion-exchangeable cation is ionexchanged by potassium ion and divalent cation in predetermined amounts. Thus, this invention provides a process for the preparation of an improved K-A type zeolite comprising the step of exchanging 33.3 to 83.3% of exchangeable cations by potassium ions and 16.7 to 66.7% of exchangeable active cations by divalent cations at an equilibrium state of ion exchange in the ion exchange of A-type zeolite wherein A-type zeolite is brought into contact with potassium ions and divalent cations in a solution or solutions, either simultaneously or separately and successively, to allow ion exchange of exchangeable cations in the A-type zeolite. The above percentage represents the equivalent percentages of potassium ions and divalent cations in the A-type zeolite.

The novel K-A type zeolite thus prepared exhibits characteristics different from those of the conventional A-type zeolite.

Differently from U.S. Pat. No. 3,078,645 the present invention teaches a superior method using an amount of exchange of 66.7 to 83.3%. The novel K-A type zeolite of the present invention does not adsorb methane, ethane or the compounds mentioned in Table C and Table D of U.S. Pat. No. 3,078,645.

Differently from U.S. Pat. No. 3,078,636 the present invention utilizes a sieving action and saturated hydrocarbon and nitrogen are not adsorbed by the novel K-A type zeolite of the present invention.

It exhibits an adsorption characteristic similar to that of the conventional K-A type zeolite for non-polar molecules and an adsorption characteristic similar to that of Ca-A type zeolite for polar molecules. As a result of the above-mentioned ion-exchanging operation, the novel K–A type zeolite changes the adsorption characteristic so that it may vary the cross-section inherently provided in the adsorptive polar molecules.

In addition, according to the present invention, polar molecules and non-polar molecules having an adsorption effective cross-section smaller than 5 A in a mixture can be separated by adsorption by bringing the solution into contact with the novel K–A-type zeolite. Prior to the adsorption process, the adsorbent is activated in a conventional manner. The aforesaid molecules having an adsorption effective crosssection of less than 5 A mean those molecules whose effective cross-section is smaller than that of those molcules which are adsorbed by 5A zeolite. The polar molecules include those molecules having unsaturated bonds, a single pair of electrons, and dipoles.

DESCRIPTION OF THE PREFERRED EMBODIMENTS

Figure 1:
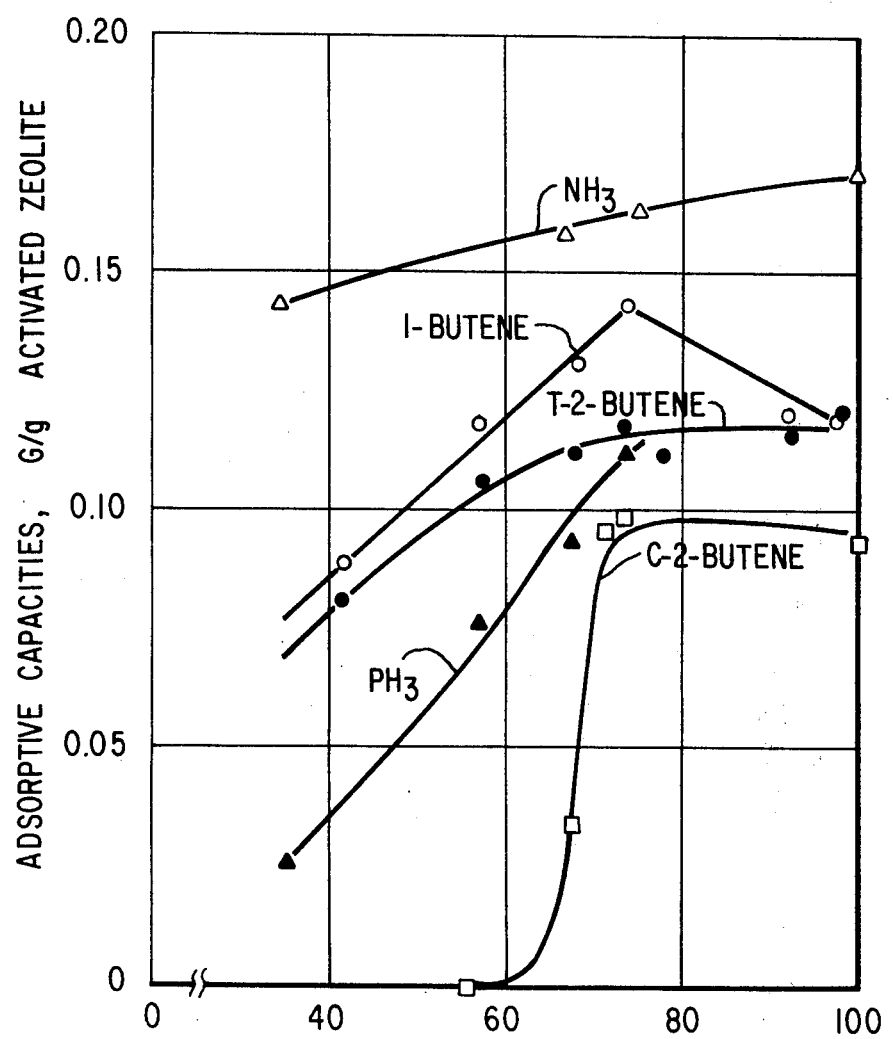
FIGS. 1 and 2 are graphs showing the adsorbtive properties of the novel K–A-type zeolite with non-polar and polar gases, respectively.

In the conventional process of the prior art, exchangeable sodium ions in Na—A type zeolite are exchanged by monovalent or divalent cations of one kind. A study tracing this process indicates that when about 16.7% of exchangeable sodium ions in the Na-A type zeolite are replaced by monovalent or divalent cations larger than sodium ions, the replaced cations begin to exhibit their characteristic, which gets stable completely when about 33.3% is replaced. The inventors discovered that the K–A zeolite in which most of exchangeable sodium ions of Na—A type zeolite are replaced by potassium ions, or the synthetic K–A zeolite, exhibit a different characteristic from that of the aforesaid Na—A type zeolite, when it is subjected to ion exchange with cations other than potassium ions. In the case of K–A type zeolite, when about 66.7% of potassium ions are replaced by divalent cations, the replaced cations begin to exhibit their different characteristic. This means that the adsorption characteristic of the A-type zeolite can be controlled for most substances, as long as about 33.3% of potassium ions are left present unchanged in the K–A type zeolite. The steps of preparing the A-type zeolite and the ion-exchange are performed by conventional means.

However, as explained above, the kind of ions to be ion-exchanged and the amount of ion exchange are strictly limited. First, the exchangeable cations in A-type zeolite are consecutively replaced by potassium ions and divalent cations, or they are replaced simultaneously using a solution containing potassium ions and divalent cations. The divalent cations in this invention are of the transition metals, e.g. zinc, cadmium, manganese, and cobalt, or the group IV metals, e.g. lead and tin.

The group II metals are particularly recommended because of their ability to replace cations in large quantities. The aforesaid metals are used in the form of chloride or nitrate for ion exchange. In order to obtain the uniform characteristic in the high-concentration ion exchange with 33.3% of potassium ions left unexchanged, the ion exchange must be completely equilibrated. As explained above, if the ion exchange ratio is below 33.3% for potassium ions and above 66.7% for divalent cations, the divalent ions exhibit their adsorption characteristic, inhibiting the effect of this invention.

Accordingly, the effect of this invention can practically be secured in a continuous manufacture by the use of the novel K–A type zeolite containing between about 40 to 75% of potassium ions and between about 25 to 60% of divalent cations in the total of 100% thereof.

In an example the ion exchange was accomplished by bringing the K–A type zeolite into contact with a mixture in solution of zinc chloride and potasssium chloride at 80°C for 12 hours. The cation exchange ratio was determined by analyzing cations in the solution and zeolite using an atomic absorption spectrophotometer. The exchanged zinc ions and potassium ions were found to be about 55% and 45%, respectively.

In the same manner a zeolite was prepared in which the ion exchange was accomplished with 50% each of zinc ions and potassium ions.

Both samples were subjected to X-ray powder diffraction after treatment in the air at 400°C, to confirm the structure of the A-type zeolite.

The above-mentioned novel A-type zeolite tends to adsorb more with the increase of exchange ratio of divalent cations. Therefore, in the following examples the exchange ratio was fixed at 50%. The same tendency was observed regardless of the kind of divalent cations exchanged.

EXAMPLE 1

Two grams of Linde M.S. 3A in which a fixed amount of water contents was adsorbed by leaving it for one week in a desiccator contained therein, and a saturated aqueous solution of ammonium chloride were brought in contact with an aqueous solution containing 1.0 g. equivalent of potassium chloride and 0.002 g equivalent of zinc chloride per one liter at 80°C for 12 hours. In the meantime, the aqueous solution was exchanged five times every two hours. The novel K–A type zeolite thus prepared was dried at 250°C. After washing several times with deionized water the zeolite was deposited in the desiccator containing the aqueous solution of saturated ammonium chloride so as to fix the adsorbed water content. Thereafter, a part of the zeolite was measured and dissolved in hydrochloric acid of two equivalent concentrations. The solution in which the zeolite was dissolved was chemically analyzed by using an atomic adsorption spectrophotometer. The result indicated that the ion-exchangeable cation of Linde M.S. 3A was 50% of potassium ion and 50% of zinc ion. Further, the adsorption characteristics of a part of said zeolite were measured by an adsorption device. Prior to introduction of gas to be adsorbed, the zeolite was kept at 350°C in vacuum and activated.

The results are given in Tables 1 and 2 below.

The same tendency as mentioned above was observed in the zeolite which was exchanged with other divalent cation in place of the above zinc ion and in the novel K–A type zeolite as described in Example 2 below.

Table 1 shows the adsorption of monosilane ($SiH_4$) and phosphine ($PH_3$) by the novel A-type zeolite.

Table 1

| Adsorbate | Temperature (°C) | Partial pressure (Torr) | Quantity adsorbed (mg) |
|---|---|---|---|
| $SiH_4$ | 0 | 160 | <2 |

Table 1-continued

| Adsorbate | Temperature (°C) | Partial pressure (Torr) | Quantity adsorbed (mg) |
|---|---|---|---|
| PH₃ | 0 | 21 | 55 |

It is noted that neither monosilane or phosphine is adsorbed by 4A zeolite but adsorbed by 5A zeolite, whereas only phosphine is adsorbed by the novel A-type zeolite. The quantity shown adsorbed in the above table indicates the quantity of adsorbate adsorbed by one gram of the adsorbent. Same applies to the next example.

Table 2 shows the adsorption of unsaturated hydrocarbons of different geometrical isomers. The 4A zeolite adsorbs all of three isomers, whereas the novel A-type zeolite adsorbs selectively 1-butene and trans-2-butene but adsorbs very little cis-2-butene. This selective adsorption has not been observed in the known adsorbent.

Table 2

| Adsorbate | Temperature (°C) | Partial pressure (Torr) | Quantity adsorbed (mg) |
|---|---|---|---|
| trans-2-Butene | 0 | 50 | 105 |
| cis-2-Butene | 0 | 50 | <2 |
| 1-Butene | 0 | 50 | 115 |

EXAMPLE 2

Two grams of Linde M.S. 4A pre-treated same as in Example 1 were used and ion-exchanged. The test on the adsorption was made by using the novel K–A type zeolite which was prepared by treating three times with an aqueous solution containing 10 g. equivalent of potassium chloride and 0.1 g. equivalent of zinc chloride per 1 liter under the same condition as in Example 1 and further treating four times with an aqueous solution containing 1 g. equivalent of potassium chloride and 0.003g equivalent of zinc chloride per 1 liter under the same condition as in Example 1. The test was carried out in the same manner as in Example 1. The ion-exchangeable cation of the novel K-A type zeolite contained 45% of potassium ion and 55% of zinc ion by equivalent percentage. The results of the test on the adsorption are given in Tables 3 and 4.

Table 3 shows the adsorption of hydrocarbons of low molecular weight. It is noted that this adsorbent adsorbs polar molecules such as propylene ($C_3H_6$), ethylene ($C_2H_4$), and carbon dioxide gas ($CO_2$). Incidentally, the 3A zeolite does not adsorb the above-mentioned substances except carbon dioxide gas. (The quantity of carbon dioxide gas adsorbed by the 3A zeolite under the same conditions as shown in Table 3 is 55 mg.) In view of the fact that this adsorbent does not adsorb methane ($CH_4$) and ethane ($C_2H_6$) but adsorbs more carbon dioxide gas than the 3A zeolite, this adsorbent is effective for the separation of saturated hydrocarbons and carbon dioxide gas.

As compared with the 3A zeolite, this novel A-type zeolite according to this invention is advantageous in that the activity decreases only a little even after the regeneration process is repeated as shown in Table 4. (More than one hundred times adsorption and regeneration were repeated for water adsorption.) Furthermore, the novel A-type zeolite of this application is not only usable for a dehydrating agent like the 3A zeolite, as shown in Table 4, but also is provided with characteristics superior to those of the conventional 3A zeolite such as of an increase in the adsorption property (the quantity adsorbed of water per unit weight) and in the durability as compared with the 3A zeolite. Thus, this invention provides an adsorbent which replaces the conventional 3A zeolite.

Table 3

| Adsorbate | Temperature (°C) | Partial pressure (Torr) | Quantity adsorbed (mg) |
|---|---|---|---|
| Propylene | 25 | 700 | 75 |
| Ethylene | 25 | 700 | 70 |
| Ethane | 25 | 760 | <2 |
| Methane | 25 | 760 | <2 |
| Carbon dioxide gas | 0 | 210 | 160 |

Table 4

| Adsorbent | Adsorption before treatment (mg) | Adsorption after treatment (mg) |
|---|---|---|
| Novel A-type zeolite | 150 | 80 |
| 3A zeolite | 135 | 45 |

Figure 2:
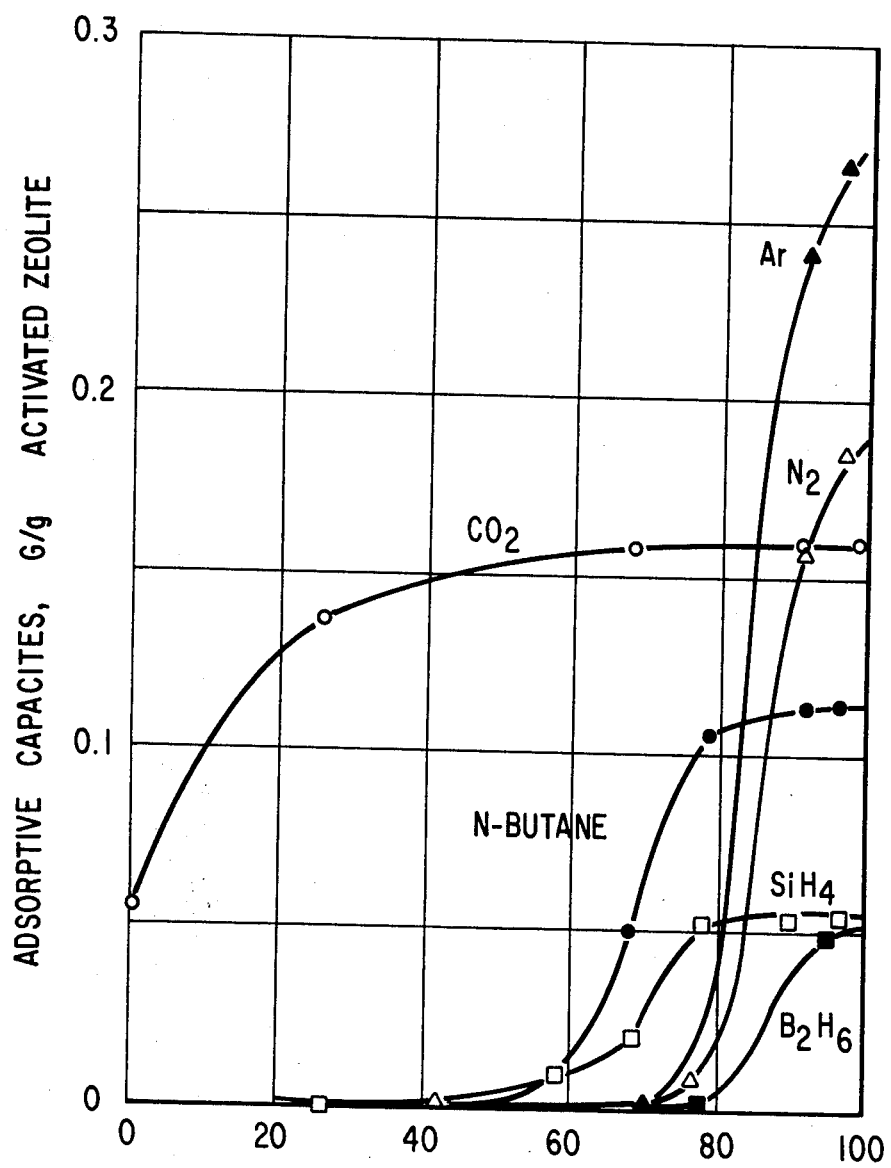

As explained in detail in the foregoing and in Examples, the novel K–A type zeolite of the present invention provides an effect which can not be obtained by the conventional zeolites. That is, although the conventional zeolites can separate the substances mentioned in the Examples, none of them can, on the one hand, avoid substantial adsorbtion, for instances, of monosilane, cis-2-butene, ethane and methane, and, on the other hand, adsorb effectively the substances, for insance, phosphine, trans-2-butene, 1-butene, propylene and ethylene. By utilizing this phenomenon of selective adsorption the novel zeolite of the present invention exhibits the most effective sieving action for separation of the mixture. It is again emphasized that the sieving action of the conventional zeolite is different from that of the novel K–A type zeolite of the present invention. The novel K–A type zeolite of the present invention provides an effective adsorption for the polar molecules. This is also understandable by reference to accompanied FIGS. 1 and 2 showing respectively the adsorption property of the typical substances and equivalent percentages of zinc ion in zeolite $$\left( \frac{2(Zn^{2+})}{(K^+) + 2(Zn^{2+})} \times 100 \text{ in zeolite} \right).$$

We claim:
1. A process for removal of phosphine from a mixture of monosilane and phosphine which comprises contacting said mixture with an improved K–A type zeolite in which approximately 33.3 to 83.3% and approximately 16.7 to 66.7% of potassium ion and zinc ion, respectively, are ion exchanged.
2. A process for removal of cis-2-butene from a mixture of unsaturated hydrocarbons, which comprises contacting said mixture with an improved K–A type zeolite in which approximately 33.3 to 83.3% and approximately 16.7 to 66.7% of potassium ion and zinc ion, respectively, are ion exchanged.
3. A process for removal of carbon dioxide from a mixture of low molecular weight saturated hydrocarbons which comprises contacting said mixture of low molecular weight saturated hydrocarbons with an im- proved K–A type zeolite in which approximately 33.3 to 83.3% and approximately 16.7 to 66.7% of potassium ion and zinc ion, respectively, are ion exchanged.

4. A process for dehydration which comprises contacting a material to be dehydrated with an improved K–A type zeolite in which approximately 33.3 to 83.3% and approximately 16.7 to 66.7% of potassium ion and zinc ion, respectively, are ion exchanged.

* * * * *